United States Patent
Barrila et al.

(10) Patent No.: US 6,696,574 B2
(45) Date of Patent: Feb. 24, 2004

(54) PROCESSES AND INTERMEDIATES FOR PREPARING GLYCOGEN PHOSPHORYLASE INHIBITORS

(75) Inventors: Mark T. Barrila, East Lyme, CT (US); Frank R. Busch, Gales Ferry, CT (US); Michel A. Couturier, Pawcatuck, CT (US); Susan L. Orrill, Gales Ferry, CT (US); Peter R. Rose, Ledyard, CT (US); Derek L. Tickner, Waterford, CT (US); Harry O. Tobiassen, Ledyard, CT (US); Gregory J. Withbroe, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 43 days.

(21) Appl. No.: 10/345,661

(22) Filed: Jan. 16, 2003

(65) Prior Publication Data

US 2003/0187051 A1 Oct. 2, 2003

Related U.S. Application Data

(60) Provisional application No. 60/349,647, filed on Jan. 18, 2002.

(51) Int. Cl.$^7$ .................. C07D 491/056; C07D 209/20
(52) U.S. Cl. ........................ 548/453; 548/467
(58) Field of Search ................. 548/453, 467

(56) References Cited

U.S. PATENT DOCUMENTS

| | | | |
|---|---|---|---|
| 6,107,329 A | 8/2000 | Hoover et al. | 514/415 |
| 6,277,877 B1 | 8/2001 | Hoover et al. | 514/415 |
| 6,297,269 B1 | 10/2001 | Hulin et al. | 514/414 |

*Primary Examiner*—Joseph K. McKane
*Assistant Examiner*—Sonya Wright
(74) *Attorney, Agent, or Firm*—Peter C. Richardson; Gregg C. Benson; Carl J. Goddard

(57) ABSTRACT

The instant invention provides novel processes and intermediates useful in the preparation of certain N-(indole-2-carbonyl)-β-alaninamide compounds, which compounds are glycogen phosphorylase inhibitors useful in the treatment of diseases such as hypercholesterolemia, hyperglycemia, hyperinsulinemia, hyperlipidemia, hypertension, atherosclerosis, diabetes, diabetic cardiomyopathy, infection, tissue ischemia, myocardial ischemia, and in inhibiting tumor growth.

2 Claims, No Drawings

PROCESSES AND INTERMEDIATES FOR PREPARING GLYCOGEN PHOSPHORYLASE INHIBITORS

This application is filed claiming priority to co-pending U.S. Provisional Application No. 60/349,647, filed Jan. 18, 2002.

FIELD OF THE INVENTION

The instant invention provides novel processes and intermediates useful in the preparation of certain N-(indole-2-carbonyl)-β-alaninamide compounds, which compounds are glycogen phosphorylase inhibitors useful in the treatment of diseases such as hypercholesterolemia, hyperglycemia, hyperinsulinemia, hyperlipidemia, hypertension, atherosclerosis, diabetes, diabetic cardiomyopathy, infection, tissue ischemia, myocardial ischemia, and in inhibiting tumor growth.

BACKGROUND OF THE INVENTION

Despite the early discovery of insulin and its subsequent widespread use in the treatment of diabetes, and the later discovery of, and use of, sulfonylureas (e.g. Chlorpropamide™ (Pfizer), Tolbutamide™ (Upjohn), Acetohexamide™ (E. I. Lilly), Tolazamide™ (Upjohn), and biguanides (e.g. Phenformin™ (Ciba Geigy), and Mefformin™ (G. D. Searle)) as oral hypoglycemic agents, therapeutic regimens for the treatment of diabetes remain less than satisfactory. The use of insulin, necessary in about 10% of diabetic patients in which synthetic hypoglycemic agents are not effective (Type 1 diabetes, insulin dependent diabetes mellitus), requires multiple daily doses, usually by self-injection. Determination of the proper dosage of insulin requires frequent estimations of sugar levels in the urine or blood. The administration of an excess dose of insulin causes hypoglycemia, with effects ranging from mild abnormalities in blood glucose to coma, or even death. Treatment of non-insulin dependent diabetes mellitus (Type 2 diabetes) usually consists of a combination of diet, exercise, oral agents, e.g., sulfonylureas, and, in more severe cases, insulin. However, clinically available hypoglycemic agents can have other side effects that limit their use. In any event, where one of these agents may fail in an individual case, another may succeed. A continuing need for hypoglycemic agents, which may have fewer side effects or succeed where others fail, is clearly evident.

Atherosclerosis, a disease of the arteries, is recognized to be the leading cause of death in the United States and Western Europe. The pathological sequence leading to atherosclerotic development and occlusive heart disease is well known. The earliest stage in this sequence is the formation of "fatty streaks" in the carotid, coronary, and cerebral arteries, and in the aorta. These lesions are yellow in color due to the presence of lipid deposits found principally within smooth-muscle cells and in macrophages of the intima layer of the arteries and aorta. It is further postulated that most of the cholesterol found within the fatty streaks, in turn, gives rise to development of the so-called "fibrous plaque", which consists of accumulated intimal smooth muscle cells laden with lipid and surrounded by extra-cellular lipid, collagen, elastin, and proteoglycans. These cells, plus matrix, form a fibrous cap that covers a deeper deposit of cell debris and more extra cellular lipid, which comprises primarily free and esterified cholesterol. The fibrous plaque forms slowly, and is likely in time to become calcified and necrotic, advancing to the so-called "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, medical professionals have placed renewed emphasis on lowering plasma cholesterol levels, and low density lipoprotein cholesterol in particular, as an essential step in prevention of CVD. The upper limits of so-called "normal" cholesterol are now known to be significantly lower than heretofore appreciated. As a result, large segments of Western populations are now recognized to be at particular high risk. Such independent risk factors include glucose intolerance, left ventricular hypertrophy, hypertension, and being male. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (high blood pressure) is a condition that occurs in the human population as a secondary symptom to various other disorders such as renal artery stenosis, pheochromocytoma, or endocrine disorders. However, hypertension is also evidenced in many patients in whom the causative agent, or disorder, is unknown. While such essential hypertension is often associated with disorders such as obesity, diabetes, and hypertriglyceridemia, the relationship between these disorders has not been elucidated. Additionally, many patients present with symptoms of high blood pressure in the complete absence of any other signs of disease, or disorder.

It is known that hypertension can directly lead to heart failure, renal failure, and stroke, which conditions are all capable of causing short-term death. Hypertension also contributes to the development of atherosclerosis, and coronary disease, which conditions gradually weaken a patient and can lead, in long-term, to death.

The precise etiology of essential hypertension is unknown, although a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in vascular constriction, and genetic pre-disposition.

The treatment of essential hypertension has been undertaken bearing the foregoing factors in mind. Thus, a broad range of β-blockers, vasoconstrictors, angiotensin converting enzyme (ACE) inhibitors, and the like have been developed and marketed as antihypertensive agents. The treatment of hypertension utilizing such agents has proven beneficial in the prevention of short-interval deaths such as heart failure, renal failure, and brain hemorrhaging (stroke). However, the development of atherosclerosis, or heart disease due to hypertension over a long period of time, remains a problem. This implies that, although high blood pressure is being reduced, the underlying cause of essential hypertension remains unresponsive to this treatment.

Hypertension has further been associated with elevated blood insulin levels, a condition known as hyperinsulinemia. Insulin, a peptide hormone whose primary actions are to promote glucose utilization, protein synthesis, and the formation and storage of neutral lipids, also acts, inter alia, to promote vascular cell growth and increase renal sodium retention. These latter functions can be accomplished without affecting glucose levels and are known causes of hypertension. Peripheral vasculature growth, for example, can cause constriction of peripheral capillaries; while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion which can occur in both out-patient and perioperative settings. There is currently an unmet medical need to prevent or minimize adverse myocardial perioperative outcomes, particularly perioperative myocardial infarction. Both cardiac and non-cardiac surgery are associated with substantial risks for myocardial infarction or death, and some 7 million patients undergoing non-cardiac surgery are considered to be at risk, with incidences of perioperative death and serious cardiac complications as high as 20–25% in some instances. In addition, of the 400,000 patients undergoing coronary by-pass surgery annually, perioperative myocardial infarction is estimated to occur in 5% and death in 1–2%. There is currently no commercial drug therapy in this area which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients. The mechanism(s) responsible for the myocardial injury observed after ischemia and reperfusion is not fully understood, however, it has been reported (M. F. Allard, et al. Am. J. Physiol., 267, H66–H74, (1994) that pre-ischemic glycogen reduction is associated with improved post-ischemic left ventricular functional recovery in hypertrophied rat hearts.

Hepatic glucose production is an important target for Type 2 diabetes therapy. The liver is the major regulator of plasma glucose levels in the post absorptive (fasted) state, and the rate of hepatic glucose production in Type 2 diabetes patients is significantly elevated relative to normal individuals. Likewise, in the postprandial (fed) state, where the liver has a proportionately smaller role in the total plasma glucose supply, hepatic glucose production is abnormally high in Type 2 diabetes patients.

Glycogenolysis is an important target for interruption of hepatic glucose production. The liver produces glucose by glycogenolysis (breakdown of the glucose polymer glycogen) and gluconeogenesis (synthesis of glucose from 2- and 3-carbon precursors). Several lines of evidence indicate that glycogenolysis may make an important contribution to hepatic glucose output in Type 2 diabetes. First, in normal post absorptive man, up to 75% of hepatic glucose production is estimated to result from glycogenolysis. Second, patients having liver glycogen storage diseases, including Hers' disease (glycogen phosphorylase deficiency), display episodic hypoglycemia. These observations suggest that glycogenolysis may be a significant process for hepatic glucose production.

Glycogenolysis is catalyzed in liver, muscle, and brain by tissue-specific isoforms of the enzyme glycogen phosphorylase. This enzyme cleaves the glycogen macromolecule releasing glucose-1-phosphate and a new shortened glycogen macromolecule. Two types of glycogen phosphorylase inhibitors have been reported to date: glucose and glucose analogs [J. L. Martin, et al., Biochemistry, 30, 10101, (1991)], and caffeine and other purine analogs [P. J. Kasvinsky, et al., J. Biol. Chem., 253, 3343–3351 and 9102–9106 (1978)]. These compounds, and glycogen phosphorylase inhibitors in general, have been postulated to be of potential use for the treatment of Type 2 diabetes by decreasing hepatic glucose production and lowering glycemia. See, for example, T. B. Blundell, et al., Diabetologia, 35 (Suppl. 2), 569–576 (1992), and Martin et al., supra.

Recently, glycogen phosphorylase inhibitors have been disclosed in, inter alia, PCT International Application Publication No. WO 97/31901, and in commonly-assigned U.S. Pat. Nos. 6,107,329, 6,277,877, and 6,297,269. The commonly-assigned U.S. Pat. Nos. 6,107,329, 6,277,877, and 6,297,269, the disclosures of which are incorporated herein by reference in their entirety, disclose novel substituted N-(indole-2-carbonyl)-β-alaninamide compounds, including 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, denoted hereinbelow as the compound of Formula (I); certain derivatives thereof; processes for the production thereof; pharmaceutical compositions comprising such compounds or such derivatives; and methods of treating glycogen phosphorylase dependent diseases or conditions by administering such compounds, such pharmaceutical compositions, or such derivatives, to a mammal in need of such treatment.

The present invention relates to improved processes useful in the preparation of the N-(indole-2-carbonyl)-β-alaninamides disclosed in the aforementioned U.S. Pat. Nos. 6,107,329, 6,277,877, and 6,297,269, including 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (I); certain intermediates related thereto; and processes useful in preparing such intermediates.

These improved processes, set forth in detail hereinbelow, provide certain advantages over those processes disclosed in the aforementioned prior art including, for example, reduced costs in preparing final products intended for human administration, minimization of impurities formed in preparing such final products, and a reduced number of synthetic steps required during the preparation of such final products.

SUMMARY OF THE INVENTION

The instant invention provides novel processes and intermediates useful in the preparation of certain N-(indole-2-carbonyl)-β-alaninamide compounds, which compounds are glycogen phosphorylase inhibitors useful in the treatment of diseases such as hypercholesterolemia, hyperglycemia, hyperinsulinemia, hyperlipidemia, hypertension, atherosclerosis, diabetes, diabetic cardiomyopathy, infection, tissue ischemia, myocardial ischemia, and in inhibiting tumor growth.

DETAILED DESCRIPTION OF THE INVENTION

The present invention provides novel processes and intermediates useful in the preparation of certain N-(indole-2-carbonyl)-β-alaninamides. More particularly, the invention provides novel processes for preparing the compound 5-chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide (I). The invention further provides intermediates useful in the preparation of the aforementioned compound, and processes for the production of such intermediates.

In one aspect of the invention, there is provided a process for preparing a compound of structural formula (I)

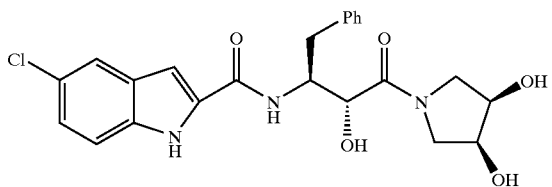

(I)

which process comprises the steps of:
(a) coupling a compound of structural formula (Ia)

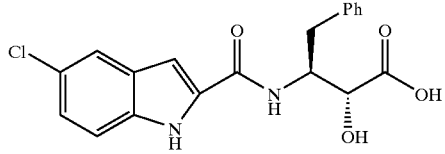

(Ia)

with 3-pyrroline to provide an amide derivative of structural formula (Ib)

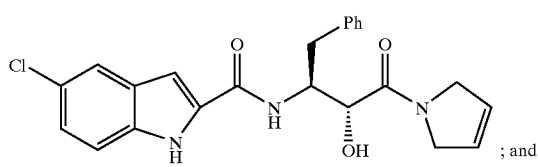

(Ib)

; and (b) oxidizing the amide derivative (Ib) formed in Step (a) to provide the compound of structural formula (I).

In the coupling reaction set forth in Step (a), the compound of structural formula (Ia)

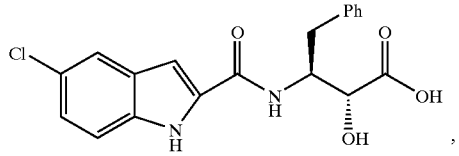

(Ia)

prepared according to the methods disclosed in the aforementioned U.S. Pat. Nos. 6,107,329, 6,277,877, and 6,297,269, is coupled with 3-pyrroline to provide the compound of structural formula (Ib)

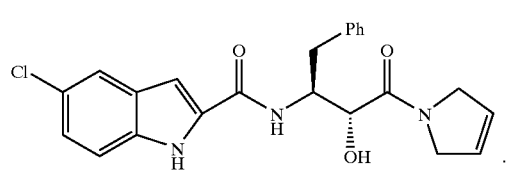

(Ib)

Such coupling reaction may be effected according to standard synthetic methodologies known to one of ordinary skill in the art. For example, such coupling may be effected using an appropriate coupling reagent such as 1-(3-dimethylaminopropyl)-3-ethylcarbodiimide hydrochloride (EDC), in the presence of 1-hydroxybenzotriazole (HOBT), 2-ethyloxy-1-ethyloxy-carbonyl-1,2-dihydroquinone (EEDQ), CDI/HOBT, propanephosphonic anhydride (PPA), or diethylphosphorylcyanide, and the like, in an aprotic, reaction-inert solvent, such as dichloromethane, acetonitrile, diethylether, tetrahydrofuran, optionally in the presence of a tertiary amine base, such as triethylamine or N,N'-diisopropylethylamine (Hunig's Base). Such coupling is typically effected at a temperature range of from about 0° C. to about the reflux temperature of the solvent employed. In a preferred embodiment, the coupling reaction is effected at ambient temperature in tetrahydrofuran using EDC, and a catalytic amount of HOBT, in the presence of an organic base selected from triethylamine or Hunig's Base. The use of Hunig's Base in such coupling is especially preferred. The 3-pyrroline starting material may be obtained from commercial sources.

The oxidation reaction set forth in Step (b) may be effected according to synthetic methodologies known to one of ordinary skill in the art for converting olefins into cis-diols. Such oxidation may be carried out using ruthenium(III) chloride, with sodium periodate as a co-oxidant, AgO (J. Org. Chem., 61, 4801 (1996)), osmium tetroxide, or a catalyst with N-methylmorpholine N-oxide (NMO) in a reaction-inert, polar organic solvent such as acetonitrile, tetrahydrofuran, alkyl ethers, and the like. In a preferred embodiment, the oxidation of (Ib) to compound (I) is effected using catalytic osmium tetroxide and N-methylmorpholine N-oxide (NMO) in tetrahydrofuran (Rosenberg, et al.; J. Med. Chem., 33, 1962 (1990)).

The product of Step (b) is then preferably isolated according to well-known methodologies known to one of ordinary skill in the art.

In another aspect, the invention provides a process for preparing a compound of structural formula (I)

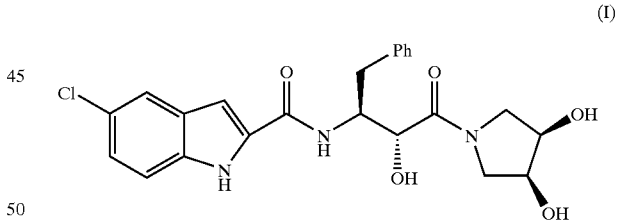

(I)

which process comprises the steps of:

(a) coupling a compound of structural formula (Ia)

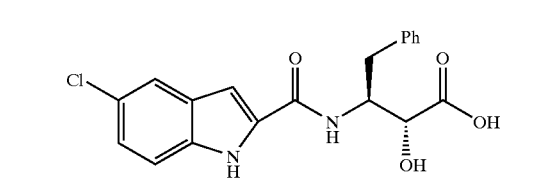

(Ia)

with (3aR,6aS)-tetrahydro-2,2-dimethyl-4H-1,3-dioxolo-[4,5-c]pyrrole, p-toluenesulfonate (IVi)

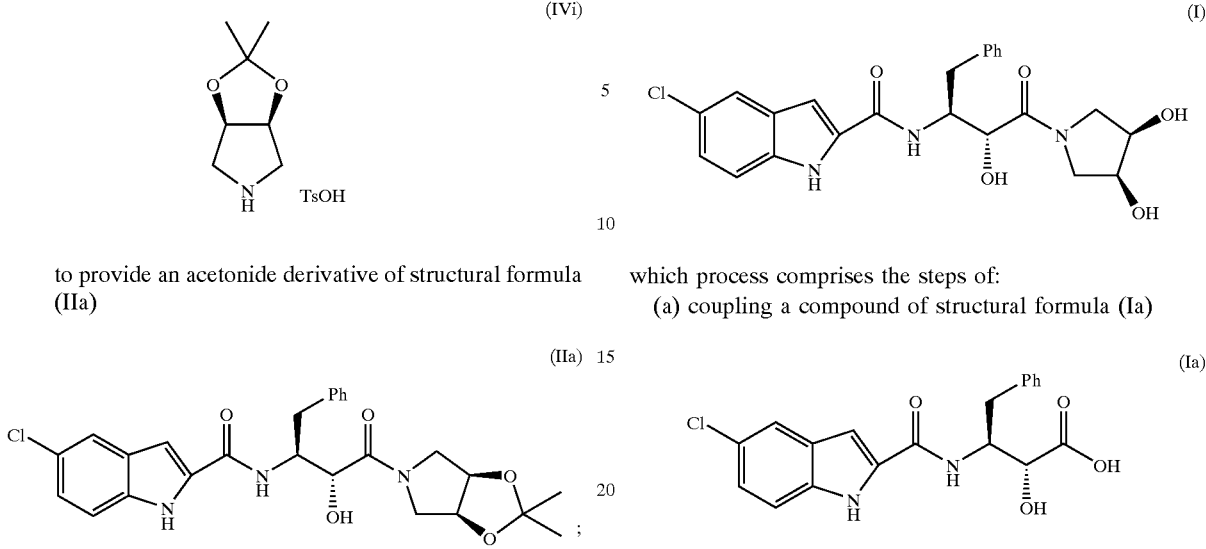

(IVi)

to provide an acetonide derivative of structural formula (IIa)

(IIa)

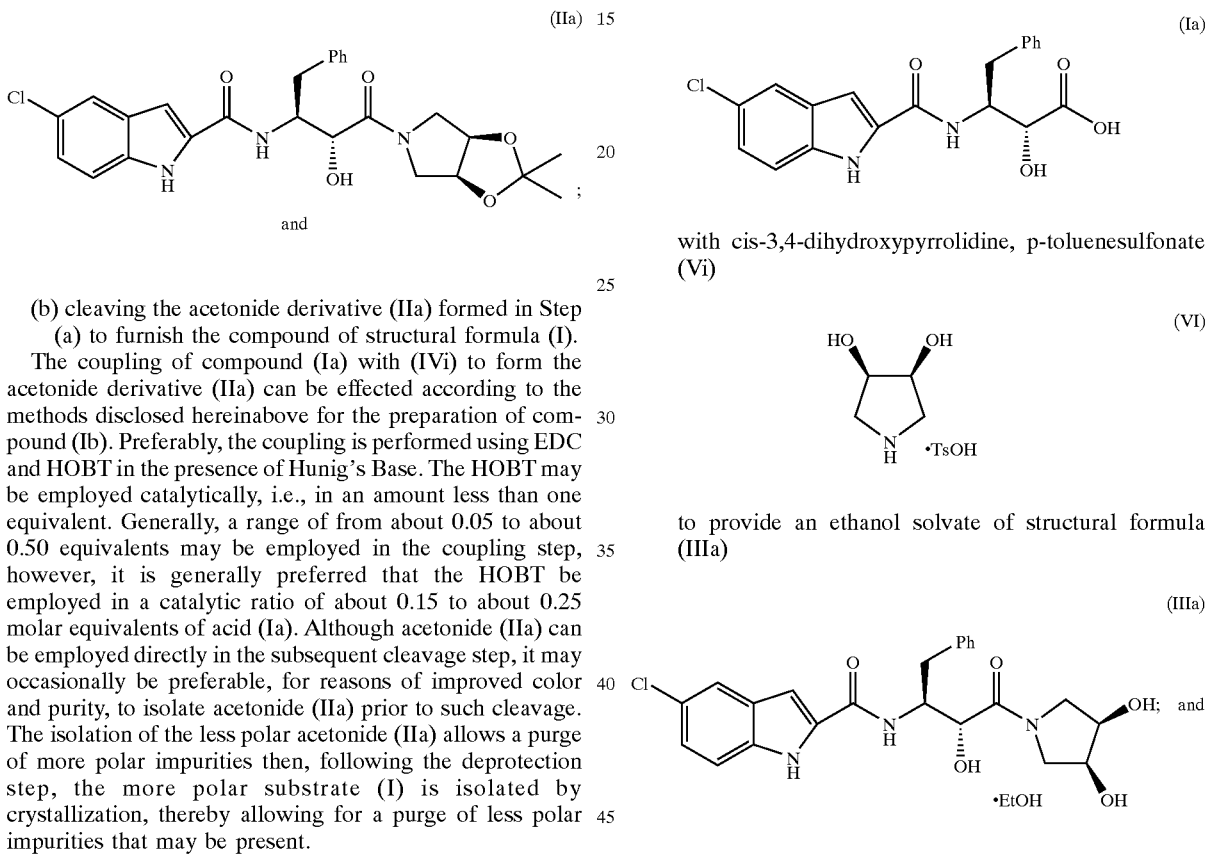

and (b) cleaving the acetonide derivative (IIa) formed in Step (a) to furnish the compound of structural formula (I).

The coupling of compound (Ia) with (IVi) to form the acetonide derivative (IIa) can be effected according to the methods disclosed hereinabove for the preparation of compound (Ib). Preferably, the coupling is performed using EDC and HOBT in the presence of Hunig's Base. The HOBT may be employed catalytically, i.e., in an amount less than one equivalent. Generally, a range of from about 0.05 to about 0.50 equivalents may be employed in the coupling step, however, it is generally preferred that the HOBT be employed in a catalytic ratio of about 0.15 to about 0.25 molar equivalents of acid (Ia). Although acetonide (IIa) can be employed directly in the subsequent cleavage step, it may occasionally be preferable, for reasons of improved color and purity, to isolate acetonide (IIa) prior to such cleavage. The isolation of the less polar acetonide (IIa) allows a purge of more polar impurities then, following the deprotection step, the more polar substrate (I) is isolated by crystallization, thereby allowing for a purge of less polar impurities that may be present.

The conversion of acetonide (IIa) into compound (I) may be effected according to generally known methods, for example, by treatment of the isolated acetonide (IIa) with a mineral acid, such as hydrochloric or hydrobromic acid, or an organic acid, such as methanesulfonic or p-toluenesulfonic acid, all in the presence of water.

Alternatively, compound (I) may also be conveniently prepared by the production, and in situ cleavage, of acetonide (IIa). The preparation of a solution of acetonide (IIa) in a suitable solvent may be effected as outlined hereinabove. The in situ conversion of acetonide (IIa) into compound (I), described in Example 5 hereinbelow, may also be conveniently effected according to known methods, for example, by treating the solution of acetonide (IIa) with an aqueous mineral acid, such as hydrochloric or hydrobromic acid, or an organic acid, such as methanesulfonic, or p-toluenesulfonic acid, also under aqueous conditions. Compound (I) so produced may then be isolated according to known preparative methods.

In another aspect of the invention, there is provided a process for preparing a compound of structural formula (I)

which process comprises the steps of:
(a) coupling a compound of structural formula (Ia)

(Ia)

with cis-3,4-dihydroxypyrrolidine, p-toluenesulfonate (Vi)

(VI)

to provide an ethanol solvate of structural formula (IIIa)

(IIIa)

(b) desolvating the ethanol solvate (IIIa) formed in Step (a) to furnish the compound of structural formula (I).

The coupling of compound (Ia) to form ethanol solvate (IIIa) may be performed according to those coupling methods previously described hereinabove for the preparation of compound (Ib) and acetonide (IIa). Preferably, the coupling is effected using EDC and HOBT in the presence of a tertiary amine base, such as triethylamine, or Hunig's Base. The use of Hunig's Base is especially preferred.

The ethanol solvate (IIIa) may be desolvated to form compound (I) by dissolving (IIIa) in an aprotic solvent, such as ethyl acetate or toluene, distilling the solution to remove residual ethanol, treating the solution with water such that a concentration of water in the range of between about 1% to about 3% water is achieved, and warming the aqueous solution to reflux temperature, at which point crystallization of (I) begins. The addition of seed crystals to the aqueous solution prior to reflux is typically preferred. The reflux period may comprise from a few hours to one or more days, preferably from about eight to about twenty hours. Once crystallization is essentially complete, excess water is removed by azeotropic distillation, preferably at atmospheric pressure, and the slurry is then cooled to between about 5° to about 30° C., preferably, about room temperature, where the isolation of (I) is performed according to standard methods, such as by filtration.

In yet another aspect, the present invention provides a process for preparing a compound of structural formula (I)

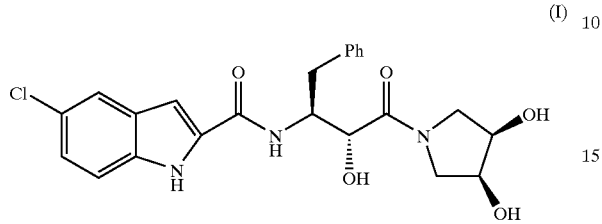

(I)

which process comprises coupling a compound of structural formula (Ia)

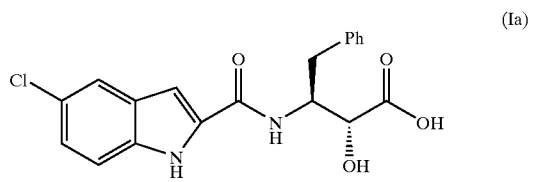

(Ia)

with cis-3,4-dihydroxypyrrolidine free base (V)

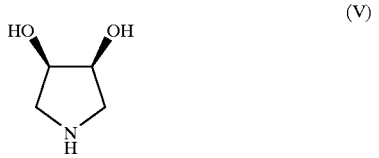

(V)

to provide the compound of structural formula (I).

The coupling of compound (Ia) with cis-3,4-dihydroxypyrrolidine free base (V) to form compound (I) may also be performed according to those coupling methods previously described hereinabove for the preparation of compound (Ib), acetonide (IIa), or ethanol solvate (IIIa). The free base of cis-3,4-dihydroxypyrrolidine (V) may be prepared according to the several synthetic methods described in detail hereinbelow including, for example, the process disclosed in Example 18. The compound of structural formula (I) so prepared is then preferably isolated according to standard methodologies that are well known to one of ordinary skill in the art.

Another aspect of the invention provides synthetic methods useful for preparing compound (V), and the acid addition salts thereof, which compound, or which acid addition salts, are intermediates useful in the preparation of compound (I). These exemplary synthetic methods are described in detail hereinbelow in Schemes 1 to 7. The cis-3,4-dihydroxypyrrolidine, p-toluenesulfonate salt (Vi) may be obtained commercially.

In one aspect, the invention provides a process useful in preparing compound (V), or an acid addition salt thereof, which process comprises the steps outlined hereinbelow in Scheme 1.

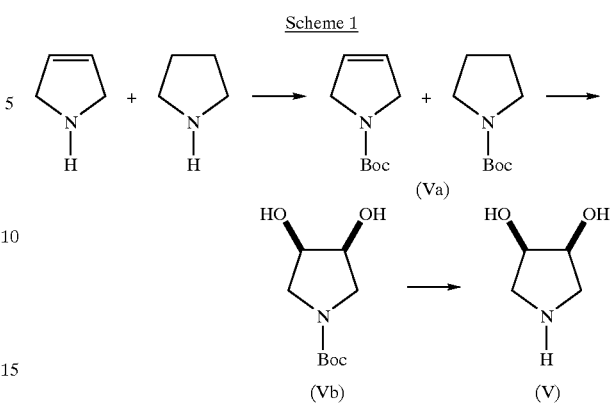

Scheme 1

As shown in Scheme 1, the 3-pyrroline starting material (Aldrich Chemical Co., Milwaukee, Wis.) is protected with BOC-anhydride in the presence of an organic or Brönsted base in an aprotic solvent. The mixture of protected N-BOC-3-pyrroline products (Va) may then be oxidized to the corresponding diol (Vb) according to known methods, for example osmium tetroxide oxidation, the use of catalytic osmium tetroxide with a co-oxidant, the use of ruthenium (III) chloride/sodium periodate (Shing, T. K. M., et al., Angew. Chem. Eur. J., 2, 50 (1996), or Shing, T. K. M., et al., Angew. Chem. Int. Ed. Engl., 33, 2312 (1994)), potassium permanganate, or similar reagents and conditions that will be well-known to one of ordinary skill in the art. The BOC protecting group of (Vb) may be subsequently removed by treatment with a suitable acid, for example, trifluoroacetic acid, methanesulfonic acid, and the like, in the presence of a reaction-inert solvent such as tetrahydrofuran, dichloromethane, or acetonitrile, to form (V).

Preferably, compound (V) is then isolated, either in the form of the free base, or in the form of an acid addition salt thereof, wherein such acid addition salt may be prepared according to known methods. Such acid addition salts, may include, for example, the hydrochloride, hydrobromide, sulfate, hydrogen sulfate, phosphate, hydrogen phosphate, dihydrogen phosphate, acetate, succinate, citrate, methanesulfonate (mesylate), and 4-methylbenzenesulfonate (p-toluenesulfonate) acid addition salts. Such acid addition salts may be prepared readily by reacting compound (V) with an appropriate conjugate acid. When the desired salt is of a monobasic acid (e.g., hydrochloride, hydrobromide, tosylate, acetate, etc.), the hydrogen form of a dibasic acid (e.g., hydrogen sulfate, succinate, etc.), or the dihydrogen form of a tribasic acid (e.g., dihydrogen phosphate, citrate, etc.), at least one molar equivalent, and usually a molar excess, of the acid is employed. However, where such salts as the sulfate, hemisuccinate, phosphate, or hydrogen phosphate are desired, the appropriate and stoichiometric equivalent of the acid will generally be employed. The free base and the acid are normally combined in a co-solvent from which the desired acid addition salt then precipitates, or can be otherwise isolated by concentration of the mother liquor, or by the precipitative effect resulting from the addition of a non-solvent. Especially preferred acid addition salts of compound (V) comprise the p-toluenesulfonate (Vi) and hydrochloride acid addition salts.

An alternative method that may be used to prepare compound (V), or an acid addition salt thereof, comprises the process outlined hereinbelow in Scheme 2.

SCHEME 2

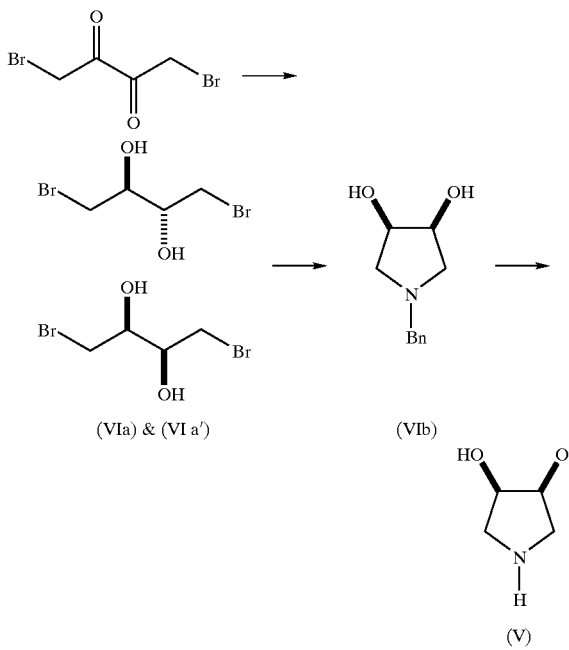

As shown in Scheme 2, the dibromo diketone starting material is reduced in the presence of a suitable reducing agent, such as sodium borohydride, in a reaction-inert solvent, such as an ether (tetrahydrofuran or methyl tert-butyl ether), or other suitable solvent(s) to provide a mixture of the syn- and anti-alcohols (VIa) and (VIa'). Alcohols (VIa) and (VIa') are then cyclized with benzylamine in the presence of a suitable base, such as sodium bicarbonate, to yield diol (VIb). The use of an additive, such as potassium iodide, has been shown to improve the rate of cyclization. See, for example, Larock, Comprehensive Organic Transformations, VCH, New York, 337–339 (1989).

The benzyl protecting group of (VIb) may be subsequently removed by standard methods, such as hydrogenation using a catalyst such as palladium on carbon in a reaction-inert solvent, such as an alcohol or ether, to form compound (V), followed by acid addition salt formation, if desired.

Yet another alternative method that may be employed in the preparation of (V), or an acid addition salt thereof, comprises the process depicted in Scheme 3.

SCHEME 3

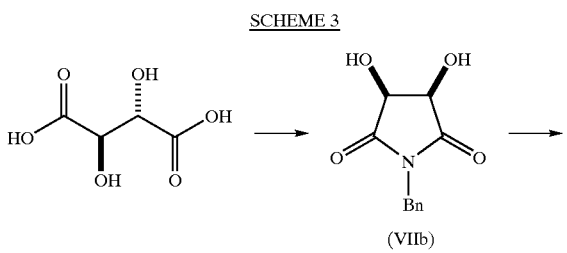

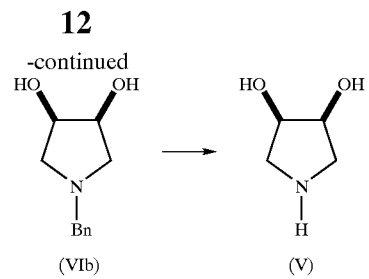

In Scheme 3, meso-tartaric acid is cyclized with benzylamine to give diol (VIIb). Such cyclization is typically effected in a reaction-inert solvent such as methylene chloride, tetrahydrofuran, or ethyl acetate at temperatures generally above ambient temperature. See, for example, March, Advanced Organic Chemistry, 4$^{th}$ Ed., Wiley Interscience, 420 (1992). It will be appreciated by one of ordinary skill in the art that such amide bond formations from carboxylic acids may be aided by addition of coupling agents such as dicyclohexylcarbodiimide, N,N'-carbonyldiimidazole, or ethyl-1,2-dihydro-2-ethoxy-1-quinolinecarboxylate (EEDQ). Diol (VIIb) is then reduced to diol (VIb) through the use of known reducing reagents, such as lithium aluminum hydride, diborane, or sodium borohydride, in the presence of boron trifluoride.

The benzyl protecting group of (VIb) may be subsequently removed by standard methods, such as hydrogenation using a catalyst such as palladium on carbon in a suitable solvent, such as an alcohol or ether, to form compound (V), followed by acid addition salt formation, if desired.

Yet another method useful in the preparation of compound (V), or an acid addition salt thereof, comprises the steps shown in Scheme 4.

SCHEME 4

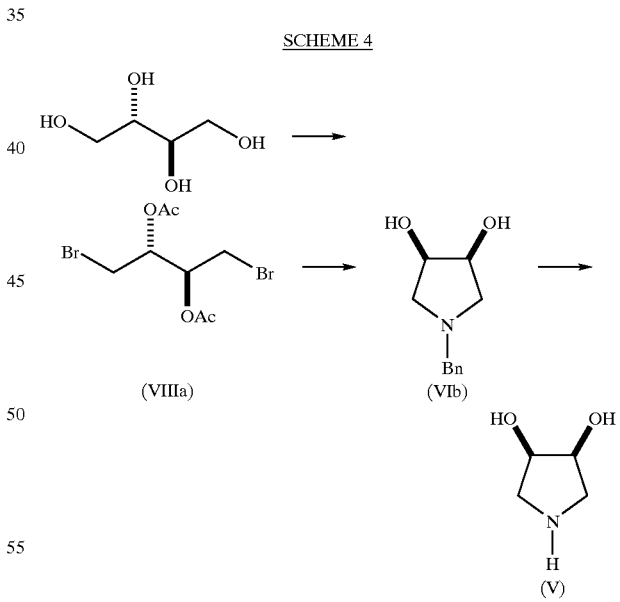

In Scheme 4, the butane-tetraol starting material is converted to diactetate (VIIa) under standard conditions, such as treatment with hydrobromic acid and acetic acid, or by those methods described in Talekar, D. G., et al., Indian J. Chem., Sect. B, 25B (2), 145–51 (1986), or Lee, E., et al., J. Chem. Soc., Perkin Trans. 1, 23, 3395–3396 (1999). Diacetate (VIIIa) is then cyclized with benzylamine in the presence of a suitable base, such as sodium bicarbonate, to give (VIb). As disclosed hereinabove, the use of an additive, such as potassium iodide, to assist cyclization may be employed if desired, or appropriate.

The benzyl protecting group of (VIb) may be subsequently removed by standard methods, such as hydrogenation using a catalyst such as palladium on carbon in a suitable solvent, such as an alcohol or ether, to form compound (V), followed by acid addition salt formation, if desired.

Yet another method useful in the preparation of (V), or an acid addition salt thereof, comprises the process shown in Scheme 5.

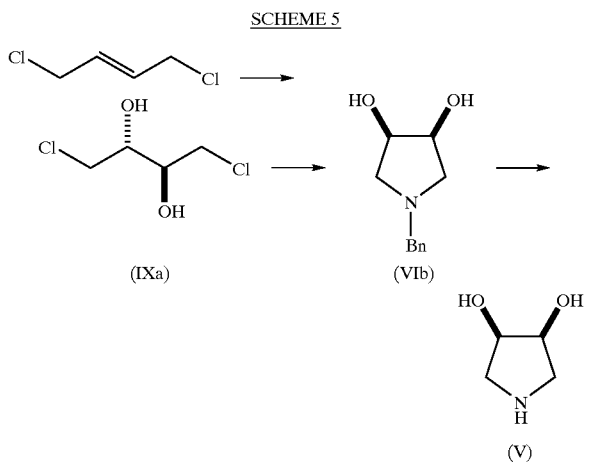

In Scheme 5, (E)-1,4-dichloro-2-butene is di-hydroxylated to furnish diol (IXa) employing conditions known to one of ordinary skill in the art, for example, hydrogen peroxide and formic acid, or m-chloroperoxybenzoic acid and water. Diol (IXa) is then cyclized with benzylamine in the presence of a suitable base, such as sodium bicarbonate, to give diol (VIb). As disclosed hereinabove, the use of an additive, such as potassium iodide, to assist cyclization may be employed if desired, or appropriate.

The benzyl protecting group of (VIb) may be subsequently removed by standard methods, such as hydrogenation using a catalyst such as palladium on carbon in a reaction-inert solvent, such as an alcohol or ether, to form compound (V), followed by acid addition salt formation, if desired.

Yet another method useful in the preparation of (V), or an acid addition salt thereof, comprises the process depicted in Scheme 6.

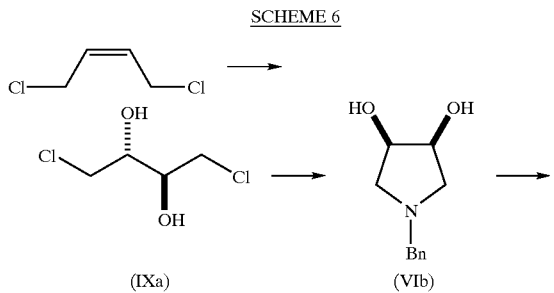

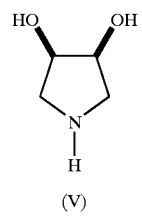

In Scheme 6, (Z)-1,4-dichloro-2-butene is di-hydroxylated to furnish diol (IXa) according to synthetic methods known to one of ordinary skill in the art. For example, such oxidation may be effected employing a mixture of sodium periodate and a ruthenium salt in a reaction-inert, aprotic solvent such as acetontrile, or a halogenated hydrocarbon solvent such as chloroform, methylene chloride, or carbon tetrachloride. Where appropriate or desired, solvent mixtures comprising reaction-inert, aprotic solvents, for example, acetonitrile and ethyl acetate, may also be utilized. In a preferred embodiment, the oxidation reaction is effected utilizing ruthenium(III) chloride hydrate and sodium periodate in a cooled acetonitrile/ethyl acetate solvent mixture. Diol (IXa) is then cyclized using benzylamine in the presence of a suitable base, such as sodium bicarbonate, to furnish compound diol (VIb). As disclosed hereinabove, the use of an additive, such as potassium iodide, to assist in cyclization may be employed if desired, and/or appropriate.

The benzyl protecting group of (VIb) may be subsequently removed by standard methods, such as hydrogenation using a catalyst such as palladium on carbon in a suitable solvent, such as an alcohol or ether, to form compound (V), followed by acid addition salt formation, if desired.

Yet another method of preparing compound (V), or an acid addition salt thereof, comprises the process shown in Scheme 7.

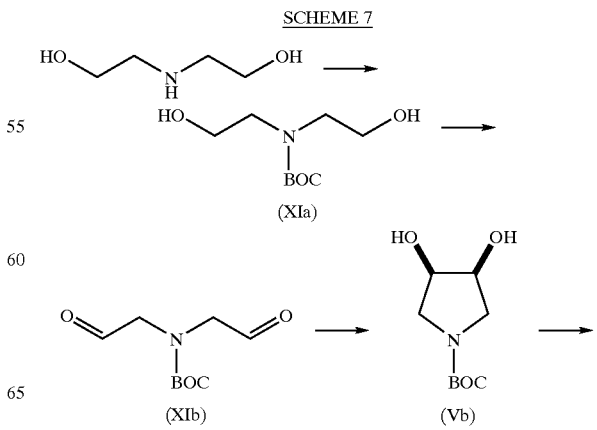

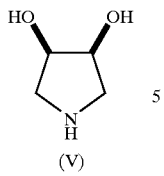

(V)

As shown generally in Scheme 7, the aminodiol starting material is protected with BOC-anhydride in the presence of an organic or Brönsted base in an aprotic solvent. The BOC protected diol (XIa) is then oxidized to dialdehyde (XIb) by methods generally known to those skilled in the art. For example, diol (XIa) may be oxidized using a strong oxidant such as potassium permanganate, ruthenium tetroxide, manganese dioxide, or Jones' reagent (chromic acid and sulfuric acid in water). Alternatively, oxidation of (XIa) to (XIb) may be effected by catalytic dehydrogenation using reagents such as copper chromite, Raney nickel, palladium acetate, copper oxide, and the like. For additional examples see, for example, March, Advanced Organic Chemistry, $2^{nd}$ edition, Wiley-Interscience, 1992. The dialdehyde (XIb) may then be cyclized to BOC-protected diol (Vb) via pinacol coupling. Known methods of effecting such coupling may comprise direct electron transfer using active metals such as sodium, magnesium, or aluminum, or through the use of titanium trichloride. The BOC-group of (Vb) can then be removed by treatment with a suitable acid as described hereinabove.

Preferably, compound (V) is then isolated, either in the form of the free base, or in the form of an acid addition salt thereof, wherein such acid addition salt may be prepared as described hereinabove.

Another aspect of the instant invention provides synthetic methods useful for preparing compound (IV) hereinbelow, and the acid addition salts thereof, which compound and acid addition salts, are also intermediates useful in the preparation of compound (I). Such exemplary synthetic methods are depicted in detail hereinbelow in Schemes 8 to 10.

In one aspect, compound (IV), or an acid addition salt thereof, may be prepared according to the process shown in Scheme 8.

SCHEME 8

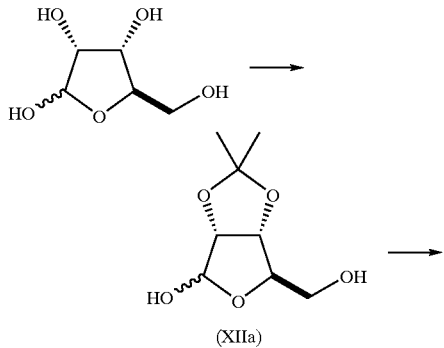

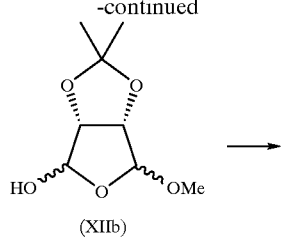

(XIIb)

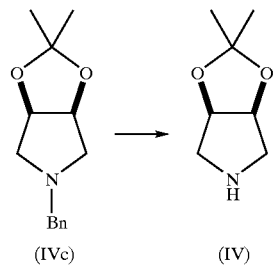

As shown in Scheme 8, ribose is protected by forming the acetonide derivative (XIIa) thereof. Such acetonide formation can be effected in a variety of ways, for example, according to those methods described in Greene, T. W., et al., Protective Groups in Organic Synthesis, $2^{nd}$ Edition, Wiley-Interscience, (1991). As an example, the formation of protected diol (XIIa) may be performed using acetone in the presence of iodine. The oxidation of (XIIa) to (XIIb) may be effected using reagents including sodium periodate in methanol. The reduction of (XIIb) may be performed according to known methods, for example, through the use of lithium aluminum hydride or sodium borohydride in the presence of acid, such as acetic acid. Amine (IVc) is prepared by treating (XIIb) with benzylamine in methylene chloride or similar reaction-inert solvents.

The benzyl protecting group of (IVc) can be subsequently removed according to standard methods, such as hydrogenation, using a catalyst such as palladium on carbon in a suitable solvent, such as an alcohol or ether, to form compound (IV).

Preferably, compound (IV) is then isolated, either in the form of the free base, or in the form of an acid addition salt thereof, wherein such acid salt may be prepared as described hereinabove. Especially preferred acid addition salts of compound (IV) are the p-toluenesulfonate (IVi) and hydrochloride acid addition salts.

Yet another method for the preparation of compound (IV), or an acid addition salt thereof, comprises the process illustrated in Scheme 9.

SCHEME 9

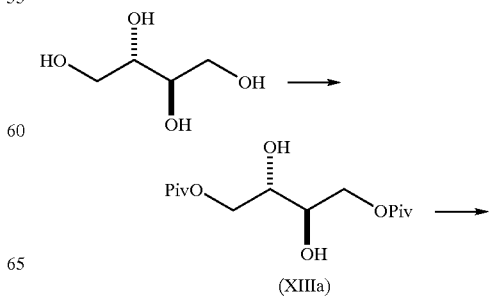

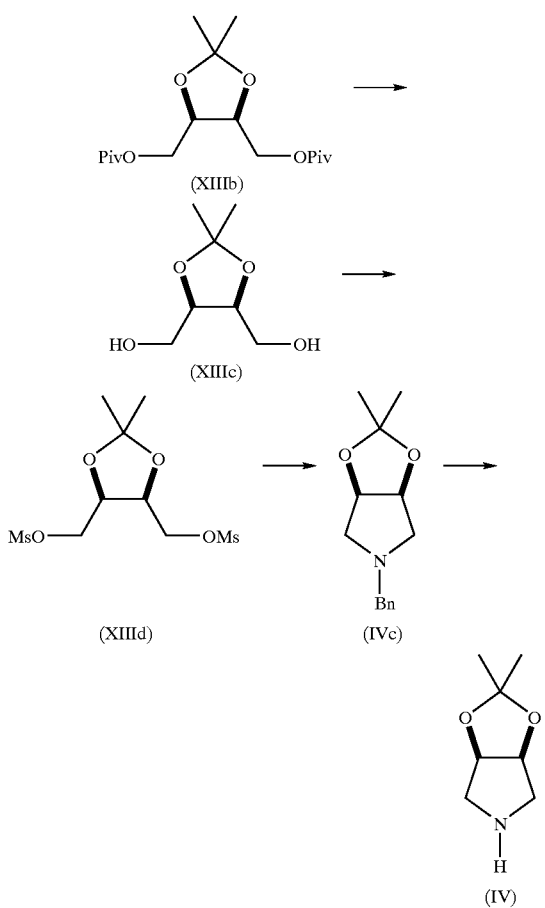

wherein Piv represents the pivaloyl moiety, i.e., $(CH_3)_3C(O)-$.

As shown in Scheme 9, meso-erythritrol is protected using standard methodologies to form the di-pivaloyl derivative (XIIIa). Such protection is preferably effected using pivaloyl chloride in the presence of a strong organic base, such as pyridine. The resulting diol (XIIIa) may be protected by formation of the acetonide (XIIIb) by treatment of (XIIIa) with tosic acid in acetone or by treatment with 2,2-dimethoxypropane (DMP). The Piv- groups of (XIIIb) may be subsequently removed according to standard methods, for example those methods disclosed in Greene, T. W., et al., Protective Groups in Organic Synthesis, $2^{nd}$ Edition, Wiley-Interscience, (1991), to form deprotected derivative (XIIIc). As an example, the deprotection of (XIIIb) may be effected using a strong inorganic base, such as sodium or potassium hydroxide, in an aqueous solvent, such as an alcohol. Mesylate activation of the diol (XIIIc), in a suitable non-reactive solvent in the presence of a base such as triethylamine, gives compound (XIIId). Cyclization of (XIIId) with benzylamine in the presence of a base, such as an organic amine, affords (IVc). The benzyl protecting group of (IVc) can be subsequently removed according to standard methods, such as hydrogenation, using a catalyst such as palladium on carbon in a suitable solvent, such as an alcohol or ether, to form compound (IV).

Preferably, compound (IV) is then isolated, either in the form of the free base, or in the form of an acid addition salt thereof, wherein such acid salt may be prepared as described hereinabove.

In another aspect, the invention provides a generally preferred process for the preparation of compound (IV), or the preferred p-toluenesulfonate acid addition salt (IVi) thereof, which process is depicted hereinbelow in Scheme 10.

Scheme 10

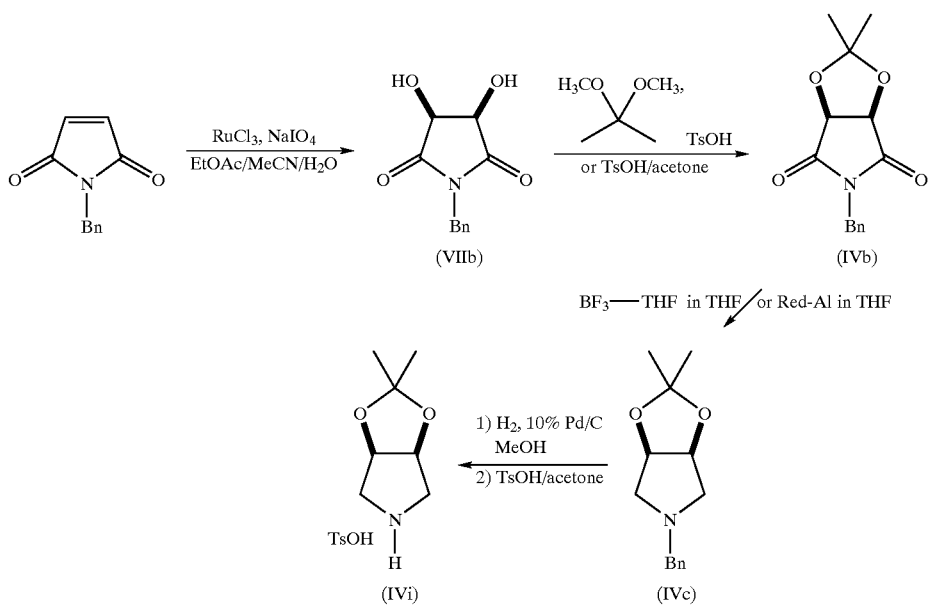

The oxidation of N-benzylmaleimide to diol (VIIb) may be performed according to synthetic methods known to one of ordinary skill in the art. For example, such oxidation may be effected employing a mixture of sodium periodate and a ruthenium salt in a reaction-inert, aprotic solvent such as acetonitrile, or a halogenated hydrocarbon solvent such as chloroform, methylene chloride, or carbon tetrachloride. Where appropriate or desired, solvent mixtures comprising reaction-inert, aprotic solvents, for example, acetonitrile and ethyl acetate, may also be utilized. In a preferred embodiment, the oxidation reaction is effected utilizing ruthenium(III) chloride hydrate and sodium periodate in a acetonitrile/ethyl acetate solvent mixture at below ambient temperature.

The formation of acetonide (IVb) may be effected according to synthetic methodologies known to one of ordinary skill in the art. For example, such protection may be performed by condensing diol (VIIb) with acetone, 2,2-dimethoxypropane, or a mixture of both, in the presence of an acid catalyst, such as sulfuric, p-toluenesulfonic, or methanesulfonic acid. In a preferred embodiment, the protection reaction is effected by condensing diol (VIIa) in 2,2-dimethoxypropane with a catalytic amount of methanesulfonic acid.

The reduction of acetonide (IVb) to (IVc) may be effected according to synthetic methodologies known to one of ordinary skill in the art. For example, such reduction may be performed using a boron or aluminum hydride complex including, for example, $BH_3THF$, $BH_3$etherate, or Red-Al® (sodium bis(2-methoxyethoxy)aluminum hydride; Aldrich Chemical Co., Milwaukee, Wis.), in an aprotic, reaction-inert solvent, such as toluene or diethylether. In a preferred embodiment, the reduction of protected acetonide (IVb) to (IVc) is effected using Red-Al® in toluene.

The deprotection of (IVc) may be effected according to synthetic methodologies known to one of ordinary skill in the art. For example, such using palladium salts, or complexes, such as $Pd(OH)_2$, or Pd/C in polar, protic solvents, such as methanol or ethanol, in a non-protic solvent, such as tetrahydrofuran, or in a mixture of such solvents. Alternatively, such deprotection may be effected under hydrogenation-transfer conditions, i.e., Pd/C with cyclohexene. In a preferred embodiment, the deprotection reaction is effected using $Pd(OH)_2$/C in methanol.

The deprotected product (IV), is then preferably isolated, in the form of the preferred p-toluenesulfonate acid addition salt (IVi) thereof, which may be either prepared as described hereinabove, or obtained commercially.

EXPERIMENTAL

The present invention is illustrated by the following Examples. It is to be understood, however, that the Examples hereinbelow are provided solely for the purpose of illustration, not limitation.

The cis-3,4-dihydroxypyrrolidine, p-toluenesulfonate salt (Vi) was purchased from Aldrich Chemical Co., Fine Chemicals Division, Milwaukee, Wis.

EXAMPLE 1

5-Chloro-N-[(1S,2R)-3-(2,5-dihydro-1H-pyrrol-1-yl)-2-hydroxy-3-oxo-1-(phenylmethyl)propyl]-1H-indole-2-carboxamide (Ib)

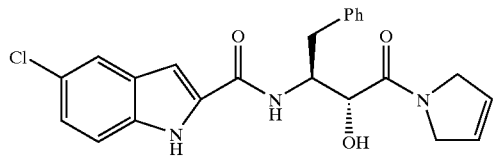

A 5.00 g (0.0134 mmol) sample of (αR,βS)-β-[[(5-chloro-1H-indol-2-yl)carbonyl]amino]-α-hydroxy-benzenebutanoic acid (Ia) (prepared according to the methods disclosed in the aforementioned U.S. Pat. Nos. 6,107, 329, 6,277,877, and 6,297,269) and 3-pyrroline (1.11 g, 0.015 mmol) (Aldrich Chemical Co., Milwaukee, Wis.) were slurried in 100 ml of tetrahydrofuran at a temperature of between 20° and 25° C. The mixture was treated with 0.6 g (0.33 equiv.) of 1-hydroxybenzotriazole hydrate (HOBT) and the mixture was cooled to between 0° and 5° C. N,N-diisopropylethylamine (2.08 ml, 2.1 equiv.) was added to the mixture over 15 minutes at 0° to 5° C. The mixture was then treated with 1-(3-dimethylaminopropyl)-3-ethylcarbodiimide hydrochloride (EDC) (2.78 g, 1.1 equiv.) at −10° to −6° C. The reaction was allowed to warm to about 20° C. and was stirred at ambient temperature for about 24 hours. The reaction mixture was treated with water (50 ml) and ethyl acetate (50 ml) to give a two-phase mixture. The layers were settled and the organic layer was separated and concentrated to furnish a solid by distillation under partial vacuum. A total of 5.1 g (92.7% yield) of the pure title product was isolated.

EXAMPLE 2

5-Chloro-N-[(1S,2R)-3-[3R,4S]-3,4-dihydroxy-1-pyrrolidinyl]-2-hydroxy-3-oxo-1-(phenylmethyl) propyl]-1H-indole-2-carboxamide (I)

(I)

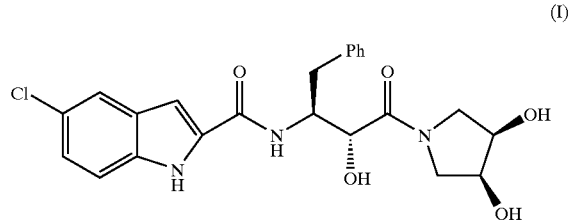

A 1.59 g (3.75 mmol) sample of (Ib), N-methylmorpholine N-oxide (413 mg, 3.52 mmol), and osmium tetroxide (3.6 g, 0.352 mmol) were combined in 15 ml of tetrahydrofuran and the resulting mixture was stirred overnight under a blanket of nitrogen. The solvent was evaporated in vacuo and the residue was partitioned between ethyl acetate and saturated aqueous sodium bicarbonate. The layers were separated, and the organic layer was washed twice with sodium sulfite solution, and then sodium bicarbonate. The aqueous washes were backwashed with ethyl acetate, dried over sodium sulfate, stirred with decolorizing charcoal, and evaporated in vacuo. The residue was adsorbed onto silica gel and flash chromatographed eluting with ethyl acetate:methanol (9:1). The product-containing fractions were combined, treated with decolorizing charcoal, and evaporated to a foam which was triturated overnight with hexanes to furnish 505 mg (25% yield) of a tan solid, m.p. 150°–155° C.

EXAMPLE 3

5-Chloro-N-[(1S,2R)]-2-hydroxy-3-oxo-1-(phenylmethyl)-3-[(3aR,6aS)-tetrahydro-2,2-dimethyl-5H-1,3-dioxolo[4,5-c]pyrrol-5-yl]propyl]-1H-indole-2-carboxamide (IIa)

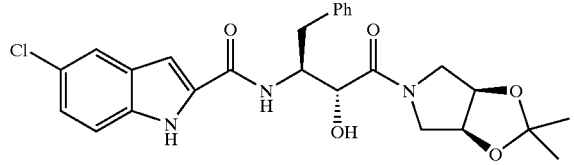

(IIa)

A 25 g (0.067 mol) amount of (Ia) and (IVI) (22.2 g, 0.0704 mol) were stirred in 125 ml of dichloromethane and 125 ml of tetrahydrofuran at 20° to 25° C. N,N-diisopropylethylamine (23.4 ml, 0.134 mole) was added to the mixture over 15 minutes at 20° to 25° C. The reaction solution was cooled to between 0° and −10° C. and treated with 1-(3-dimethylaminopropyl)-3-ethylcarbodiimide hydrochloride (EDC) (14.2 g, 0.0741 mol), and hydroxybenzotriazole hydrate (HOBT) (10.0 g, 0.074 mol). The reaction mixture was stirred at −6° to −10° C. for about 30 minutes. The reaction was allowed to warm to ambient temperature over about 45 minutes and stirred for about 2 hours. The reaction mixture was treated with 50% aqueous sodium hydroxide to give a pH of about 10, and the two-phase mixture was allowed to settle. The organic layer was concentrated to an oil by rotary evaporation using partial vacuum. A total of 31 g (88% yield) of title compound was isolated.

EXAMPLE 4

5-Chloro-1H-indole-2-carboxylic acid-[(1S-benzyl-3-((3R,4S)-dihydroxy-pyrrolidin-1-yl)-(2R)-hydroxy-3-oxopropyl]-amide (I)

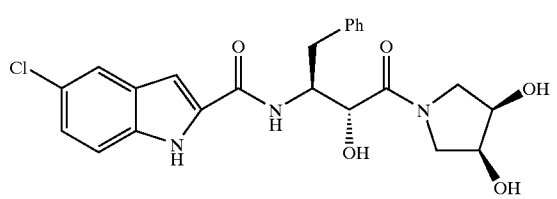

(I)

A 2.0 g sample of acetonide (IIa) was dissolved in a mixture of 10 ml tetrahydrofuran and 10 ml of water. The pH was adjusted to 1.8 with 6N hydrochloric acid, and the solution was heated to reflux. After refluxing overnight, the pH was adjusted to about 7 to 8 with 50% sodium hydroxide, and the mixture was atmospherically distilled to remove the tetrahydrofuran. The layers were separated, the organic layer was washed with 10 ml of water, and to the combined organic layers were added 25 ml of heptane. The resulting white crystalline precipitate was stirred for about one hour, collected by filtration, and washed with heptane. The solid was dried overnight in vacuo to provide 1.7 g of the title compound.

EXAMPLE 5

5-Chloro-1H-indole-2-carboxylic acid-[(1S-benzyl-3-((3R,4S)-dihydroxy-pyrrolidin-1-yl)-(2R)-hydroxy-3-oxopropyl]-amide (I)

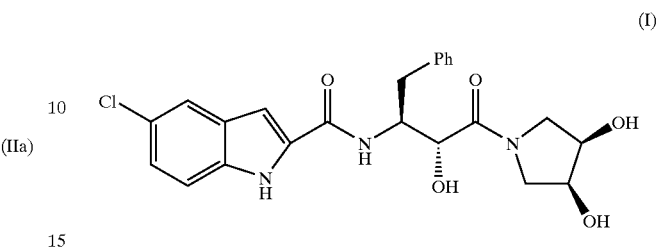

(I)

A 10 g (0.027 mole) sample of (Ia), an 8.88 g (0.028 mole) sample of (IVi) and 0.06 g (0.044 mole) of HOBT were combined in 50 ml of tetrahydrofuran, and the resulting slurry was cooled to −10° to −5° C. A total of 4.15 g (0.032 mole) of Hunig's Base, and 5.66 g (0.03 mole) of EDC were added and the resulting solution was stirred at ambient temperature for about 12 hours. The solution was diluted with 50 ml of water, and the pH was adjusted to about 1.7 using 1.5 ml of concentrated HCl. The reaction mixture was then heated to reflux for about 10 hours. The pH was adjusted to 6.5 to 7.5 with 50% sodium hydroxide, and the solution was reduced to a small volume by atmospheric distillation at a pot temperature of about 90° C. A total of 100 ml of ethyl acetate was added, the organic layer was washed with 50 ml of water, and the organic layer was diluted with 50 ml of toluene. The mixture was refluxed overnight, stirred for about 10 hours at ambient temperature, and filtered. The residual solid was dried in vacuo at a temperature of about 45° C. to afford 10.4 g (86.6% yield) of the title product.

EXAMPLE 6

5-Chloro-N-[(1S,2R)-3-[3R,4S]-3,4-dihydroxy-1-pyrrolidinyl]-2-hydroxy-3-oxo-1-(phenylmethyl)propyl]-1H-indole-2-carboxamide, ethanolate (IIIa)

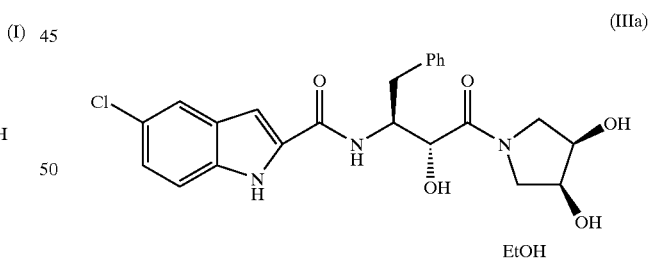

(IIIa)

A 53 kg (142.2 mol) sample of (Ia) was suspended in 35 gallons of N,N-dimethylformamide. The resulting mixture was treated with ethyl acetate (70 gallons) and cooled to between 0° to 5° C. The cooled mixture was treated in order with N,N-diisopropylethylamine (36.6 kg, 284.3 mol), 1-(3-dimethylaminopropyl)-3-ethylcarbodiimide hydrochloride (30 kg, 156.4 mol), and 1-hydroxybenzotriazole hydrate (24 kg, 156.38 mol). The reaction mixture was then treated with cis-3,4-dihydroxypyrrolidine, p-toluenesulfonate (Vi) (41.1 kg, 149.3 mol) and the reaction was allowed to stir for about 30 minutes at 0° to 5° C. The reaction was then warmed to ambient temperature and stirred for about 6 hours. The reaction mixture was treated with water (175 gallons), stirred for about 1 hour, and then allowed to settle. The aqueous layer was separated off and was washed twice with ethyl acetate (2×35 gallons). The ethyl acetate layers were combined and washed three times with aqueous sodium bicarbonate (2×23.8 kg sodium bicarbonate in 70 gallons of water and 1×11.9 kg sodium bicarbonate in 35 gallons of water). The ethyl acetate solution was combined with 20 gallons of ethyl acetate and 35 gallons of water, stirred for about 30 minutes and then allowed to settle. The ethyl acetate layer was separated off, treated with decolorizing charcoal (0.55 kg), and then stirred for about 15 minutes. The mixture was filtered to remove the charcoal and the solution was concentrated in vacuo to a volume of about 80 gallons. The ethyl acetate was displaced by distillation using ethanol (4×55 gallons), whereupon a thick white slurry formed at a final volume of about 110 gallons. The product was stirred at ambient temperature for about 18 hours. A total of 83.2 kg of the title compound was isolated by filtration as an ethanol-wet cake.

EXAMPLE 7

5-Chloro-1H-indole-2-carboxylic acid-[(1S-benzyl-3-((3R,4S)-dihydroxy-pyrrolidin-1-yl)-(2R)-hydroxy-3-oxopropyl]-amide (I)

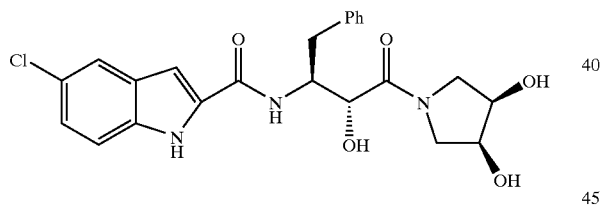

(I)

A 74 kg sample of (IIIa) and 88 gallons of ethyl acetate were combined and the resulting slurry was stirred at ambient temperature until a complete solution was obtained. The mixture was concentrated by atmospheric distillation until about 44 gallons of distillate had been collected (distillate refractive index=1.3716). A thick white slurry, formed upon cooling below about 40° C. Water (6.1 l) was added to the slurry to form an almost clear solution, and then hexanes (54 gallons) was added over a period of between 2 and 3 hours. The resulting slurry was stirred at ambient temperature for about 2.5 days. The solids were filtered off, washed with ethyl acetate (8 gallons), and then blown dry under a nitrogen stream. The solid was dissolved in ethyl acetate and the solution was stirred at ambient temperature for about 11 days, whereupon a solid product gradually formed. The solid was then filtered off and vacuum dried at 30° to 45° C. to give the title compound (30.9 kg, 71.6% yield).

EXAMPLE 8 cis-3,4-Dihydroxy-2,5-pyrrolidinedione (VIIb)

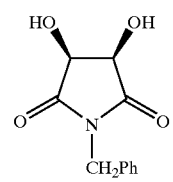

(VIIb)

A solution of N-benzylmaleimide (50.0 kg), in 125 L of acetonitrile and 859 L of ethyl acetate was combined with an aqueous mixture of 0.499 kg of ruthenium (III) chloride hydrate in 352 L of water, and the resulting reaction mixture was cooled to about 5° C. Sodium periodate (74.4 kg) was added with stirring to the reaction solution in small portions, while maintaining the reaction temperature between 3° C. and 5° C. Once the addition was complete, the reaction was quenched with an aqueous solution of sodium thiosulfate (45 kg) in 38 L of water, and the resulting slurry was granulated for about 20 minutes. The inorganic salts were removed by suction filtration, and the filter cake was washed with ethyl acetate. The combined filtrates were washed with water and allowed to settle. The aqueous layer was extracted with ethyl acetate and the product-rich organic layers were combined and washed with a solution of 8 kg of sodium chloride in 72 L of water. The organic extracts were concentrated by atmospheric distillation at a temperature of about 75° C., cooled to room temperature, and allowed to granulate for 2 to 4 hours. Hexanes (360 L) was added to the cooled (5° C. to 15° C.) slurry and granulation was continued for about 1 hour. The precipitated solids were collected by suction filtration, washed well with ethyl acetate followed by hexanes, and then dried in vacuo at a temperature of about 40° C. to about 45° C. to provide the title compound (42.0 kg, 71% yield) as a white solid.

EXAMPLE 9

(3aR,6aS)-Dihydro-2-dimethyl-5-(phenylmethyl)-4H-1,3-dioxolo[4,5-c]pyrrole-4,6(5H)-dione

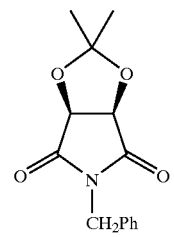

(IVb)

To a slurry of 58.6 kg of (IVa) in 117.2 L of 2,2-dimethoxypropane was added 1.72 L of methanesulfonic acid and the reaction mixture was stirred at room temperature for 6 to 9 hours until the reaction was complete. A total of 322 L of diisopropyl ether was added to the reaction mixture and the resulting slurry was granulated. After cooling to −10° to −15° C., the granulation was continued for an additional 2 hours. The precipitated solids were collected by filtration, washed with diisopropyl ether, and dried under vacuum for about 12 hours at 40 to 45° C. to provide the title compound (57.8 kg, 84% yield).

EXAMPLE 10

(3aR,6aS)-Tetrahydro-2,2-dimethyl-5-(phenylmethyl)-4H-1,3-dioxolo-[4,5-c]pyrrole (IVc)

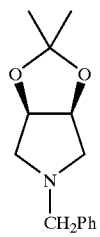

(IVc)

A total of 56.1 kg of (IVb) and 563 L of toluene were combined and the mixture was warmed to between 50° C. and 60° C. until an almost complete solution had been achieved. The resulting solution was filtered to remove some trace insolubles and was then added to a solution of 277.6 kg of Red-Al® (65 wt. % solution of bis(2-methoxyethoxy) aluminum hydride in toluene) in 141 L of toluene. The resulting solution was heated to reflux for about 4 hours and was then cooled to about room temperature. To the reaction solution was slowly added a solution of 224 L of a 50% aqueous solution of sodium hydroxide in 623 L of water, while carefully maintaining an internal temperature of between 10° C. and 30° C. Following addition, the mixture was stirred for about 20 minutes and the layers were allowed to settle. The organic layer was washed twice with 74 gal. portions of water, dried, and the toluene was removed by atmospheric distillation, displacing with methanol. The resulting oil (93% yield) was employed directly in the next step.

EXAMPLE 11

(Alternate Preparation)

(3aR,6aS)-Tetrahydro-2,2-dimethyl-5-(phenylmethyl)4H-1,3-dioxolo-[4,5c]pyrrole (IVc)

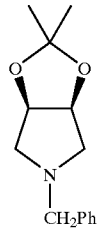

(IVc)

A solution of 47.5 kg of (IVb) in 378.5 L of tetrahydrofuran was concentrated to about ¾ volume by distillation, cooled, and sampled for water content. While maintaining a temperature of between 10° C. and 20° C., a total of 263 kg of borane-tetrahydrofuran complex (2M in tetrahydrofuran) was added under nitrogen at a rate of about 1.0 kg/minute. The reaction mixture was allowed to stir at room temperature for about 4 hours, after which time the reaction was quenched by the addition of 238.5 ml of methanol while maintaining a temperature of 10° C. and 20° C. during the addition. Following the methanol addition, the mixture was stirred for about 1 hour at room temperature, then at 35° to 45° C. for about 2 hours, and then to reflux temperature where the tetrahydrofuran was displaced with methanol by concentrating the reaction mixture to about 145 L via atmospheric distillation at a temperature of 55° C. to 65° C. The mixture was cooled to 30° C. and 50° C., 473 L of methanol was added, and the mixture was concentrated to a final volume of about 145 L again by atmospheric distillation as previously described. The concentrate was cooled to about room temperature and about 1 L of water was added. The resulting solution of the title compound was used directly in the following step.

EXAMPLE 12

(3aR,6aS)-Tetrahydro-2,2-dimethyl-4H-1,3-dioxolo-[4,5-c]pyrrole, p-toluenesulfonate (IVi)

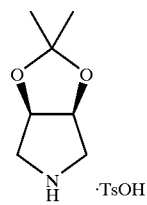

(IVi)

A 195 L sample of (IVc) was combined in a hydrogenation vessel with 7.1 kg of 20% palladium hydroxide on carbon (50% water wet), and the mixture was hydrogenated at about 50 psig for about 10 hours at about 20° C. Upon reaction completion, the mixture was filtered to remove the catalyst, and the filter cake was washed well with methanol. The reaction mixture was concentrated by atmospheric distillation to a volume of about 80 L and 288 L of methyl ethyl ketone was added. The solution was reduced in volume to about 133 L by atmospheric distillation, and the solution filtered. The resulting solution was then treated, over a time period of about 1 hour, with a solution of 34.6 kg of p-toluenesulfonic acid in 102 L of methyl ethyl ketone and the mixture was allowed to granulate for about 5 hours at 10° C. to 20° C. The slurry was cooled to between 0° C. and 5° C., and granulated for a further 2 hours. The precipitated product was collected by filtration, washed with cold methyl ethyl ketone, and dried in vacuo at 40° C. to 45° C. to furnish the title compound (44.8 kg, 74% yield) as a white crystalline solid.

EXAMPLE 13

3,4-O-Isopropylidene-D-ribofuranose (XIIa)

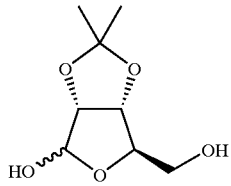

(XIIa)

To a 500 ml flask equipped with a magnetic stir bar was charged D-ribose (20.0 g, 0.13 mol). Acetone (200 ml) was added and stirring was commenced. Iodine (0.01 g, 0.40 mmol) was added and the solution was stirred at room temperature until a clear brown solution was obtained. Sodium thiosulfate (0.50 g, 3.16 mmol) was added and the slurry stirred until the solution had become colorless. Diatomaceous earth (5.00 g) was added to the slurry and the mixture was filtered. The filtrate was concentrated in vacuo affording 25.0 g (99% yield) of the title compound as a thick yellow oil, which was used directly without further purification.

Thin layer chromatographic analysis (ethyl acetate; silica gel; visualized with phosphomolybdic acid) indicated four spots: $R_f$=0.89, 0.72 major (product), 0.38, and 0.00.

$^1$H NMR (300 MHz; CDCl$_3$): δ6.47 (d, 1H), 5.32 (d, 1H), 4.96 (t, 1H), 4.82 (d, 1H), 4.53 (d, 1H), 4.32 (m, 1H), 3.64 (m, 2H), 1.48 (s, 3H), 1.32 (s, 3H)

EXAMPLE 14

3,4-O-Isopropylidene-2-hydroxy-5-methoxyfuran (XIIb)

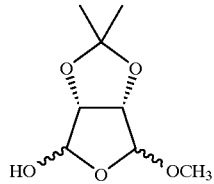

(XIIb)

To a three-necked flask equipped with a reflux condenser, mechanical stirrer, and a temperature controller, was added (XIIa) (20.0 g, 0.11 mol), and anhydrous methanol (500 ml). The stirred reaction mixture was then placed under a nitrogen atmosphere. Sodium periodate (44.8 g, 0.21 mol) was added and the stirred mixture was heated to about 40° C. overnight. The solution was allowed to cool to room temperature, diatomaceous earth (10 g) was added, and the slurry was filtered. The resulting filtrate was concentrated to a thick oil which was dissolved in 300 ml of methylene chloride. The resulting filtrate was washed successively with saturated aqueous sodium bicarbonate (200 ml), 2% aqueous sodium thiosulfate (200 ml), and saturated aqueous sodium chloride (200 ml). The organic layer was dried over magnesium sulfate, filtered, and concentrated in vacuo to afford 13.2 (66% yield) of the title compound as a yellow oil. This material was used directly without further purification.

Thin layer chromatographic analysis (1:1 ethyl acetate/hexanes; silica gel; visualized with phosphomolybdic acid) indicated two spots: $R_f$=0.82, 0.66 major (product).

$^1$H NMR (300 MHz; CDCl$_3$) [diasteriomeric mixture]: δ5.43 (2s), 5.41 and 5.28 (2d), 5.05 (s, 1H), 4.85 (s, 1H), 4.68 (m, 1H), 3.98 and 3.98 (s), 3.43 (s, 3H), 3.36 (s, 3H), 1.53 (s, 3H), 1.38 (s, 3H), 1.47 (s, 3H), 1.32 (s, 3H).

EXAMPLE 15 cis-3,4-O-Isopropylidene-N-benzyl-pyrrolidine (IVc)

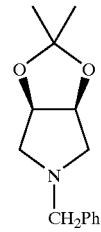

(IVc)

Methylene chloride (400 ml) was charged to a three-necked flask equipped with a pressure equalizing addition funnel, mechanical stirrer, and thermometer. Sodium borohydride (7.20 g, 0.19 mol) was added, stirring was commenced, and the slurry was cooled to about 5° C. with an ice bath. Acetic acid (37.1 g, 0.62 mol) was added dropwise over about 45 minutes. The cooling bath was removed and the reaction mixture was allowed to warm to room temperature where it was allowed to stir for about two hours. Benzylamine (7.10 g, 0.07 mol) was added, followed immediately by the addition of a solution of (XIIb) (12.0 g, 0.63 mol) in 30 ml of methylene chloride. The solution was stirred overnight at room temperature. The reaction was quenched with saturated aqueous sodium bicarbonate solution (200 ml), and the resulting bi-phasic mixture was stirred vigorously for about thirty minutes. The organic layer was separated and the aqueous layer was extracted with methylene chloride (200 ml). The combined organic extracts were washed successively with saturated aqueous sodium bicarbonate (200 ml), and 10% aqueous sodium chloride (200 ml). The combined organic extracts were dried over magnesium sulfate, filtered, and concentrated in vacuo. This afforded 14.5 g (98.6% yield) of the title compound as a yellow oil.

Thin layer chromatographic analysis (20% ethyl acetate/hexanes; silica gel; visualized with phosphomolybdic acid) indicated two spots: $R_f$=0.36 major (product), 0.02.

$^1$H NMR (300 MHz; CDCl$_3$): δ7.2–7.4 (m, 5H), 4.65 (d, 2H), 3.62 (s, 2H), 3.06 (d, 2H), 2.17 (dd, 2H), 1.58 (s, 3H), 1.32 (s, 3H).

EXAMPLE 16 cis-3,4-Dihydroxy-N-benzyl-pyrrolidine, hydrochloride (VIb)

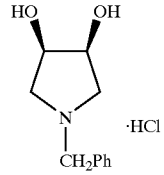

(VIb)

To a round-bottomed flask equipped with a reflux condenser and a magnetic stirring bar was added (IVd) (5.00 g, 0.02 mol). Ethanol (10 ml) was added and stirring was commenced. Concentrated hydrochloric acid (7 ml, 0.09 mol) was added and the solution was heated to reflux. After about four hours, the solution was allowed to cool to room temperature and concentrated in vacuo to afford a thick oil. Ethanol (10 ml) was added and the resulting solution was stirred at room temperature. Isopropyl acetate (35 ml) was added dropwise resulting in crystallization of the product. The slurry was stirred overnight, filtered, and the filter cake was washed with isopropyl acetate (20 ml). The filter cake was dried overnight at room temperature under reduced pressure (about 30 mm Hg) to afford 2.7 g (56% yield) of the title compound as an off-white solid, m.p. 122–123° C.

$^1$H NMR (300 MHz; CDCl$_3$): δ7.58 (m, 2H), 7.45 (m, 3H), 5.48 (br d, 2H), 4.38 (d, 1H), 4.32 (br s, 2H), 4.25 (br s, 1H), 4.08 (br s, 1H), 3.42 (m, 1H), 3.32 3.13 (m, 1H), 302 (m,1H).

EXAMPLE 17 cis-3,4-Dihydroxypyrrolidine (V)

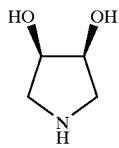

(V)

A 3.34 kg sample of (VIb) was dissolved in 1.8 L of ethyl acetate and added to a mixture of 669 g of 10% Pd/C (50% water wet) in 9 gallons of methanol. The resulting mixture was hydrogenated with agitation at a pressure of about 50 psi for about 73 hours. The catalyst was removed by filtration, and the filter cake was rinsed with methanol. The filtrate was concentrated in vacuo to 1.98 kg of thick, amber-colored oil that partially crystallized. To the oily residue was added about 2 L of isopropanol, and the suspension was azeotropically distilled to remove residual traces of water, resulting in the collection of about 1 L of distillate. An additional 1 L of isopropanol was added and the resulting suspension was stirred at ambient temperature for about 48 hours. The mixture was filtered, the collected solid was washed with 420 ml of isopropanol, and the product dried in vacuo at ambient temperature to furnish 826 g of the title free base as a hygroscopic white solid, m.p. 108°–119° C. An additional 97 g of product was obtained from the concentrated filtrate.

$^1$HNMR (DMSO-d$_6$): δ2.46–2.51 (m, 2H, 2'H, 5'H), 2.81–2.87 (m, 2H, 2"H, 5"H), 3.30 (br s, 1H, 1-NH), 3.74–3.77 (m, 2H, 3-H, 4-H), 4.39 (br s, 2H, both OH).

$^{13}$C NMR (DMSO-d$_6$) δ52.62, 71.93.

Anal. Calc'd, for C$_4$H$_9$NO$_2$: C, 46.59; H, 8.80; N, 13.58. Found: C, 46.62, H, 9.36; N, 13.43.

Example 18

5-Chloro-N-[(1S,2R)-3-[3R,4S]-3,4-dihydroxy-1-pyrrolidinyl]-2-hydroxy-3-oxo-1-(phenylmethyl) propyl]-1H-indole-2-carboxamide (I)

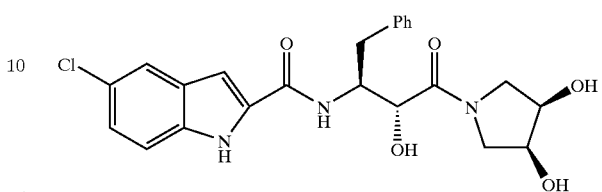

(I)

A 3.05 kg amount of (Ia) was dissolved in a mixture of 6.1 L of dimethylformamide and 4 gallons of ethyl acetate. The reaction solution was cooled to between 0° and 5° C. and treated with hydroxybenzotriazole hydrate (HOBT) (1.38 kg), followed by 1-(3-dimethylaminopropyl)-3-ethylcarbodiimide hydrochloride (EDC) (1.72 kg). While maintaining the internal temperature at about 5° C., a total of 884.4 g of cis-3,4-dihydroxypyrrolidine free base (V) was added, and the reaction was allowed to stir at ambient temperature for about 15 hours. The reaction was then cooled to between 10° and 15° C., and quenched slowly with 39 L of water. The lower, product layer was removed and the aqueous layer was then washed with about 2 gallons of ethyl acetate. The organic and product layers were combined and washed three times with sodium bicarbonate solutions (one wash with a solution of 1.37 kg sodium bicarbonate in 4 gallons water, followed by two washes with a solution of 687 g sodium bicarbonate in 2 gallons water). The organic layer was treated with decolorizing charcoal, filtered, and the residue washed with 1 gallon of ethyl acetate. The filtrate was concentrated to a volume of about 2 gallons, diluted with 16 L of ethanol, and then concentrated in vacuo to a volume of about 8 L. An additional 10 L of ethanol was added, and the resulting suspension was stirred overnight. An additional 10 L of ethanol was added, and the mixture was filtered. The collected solid was washed with 3 L of ethanol, and dried in vacuo at a temperature of about 35° C. to furnish 2.47 kg of the title compound.

We claim:
1. A compound of the structural formula

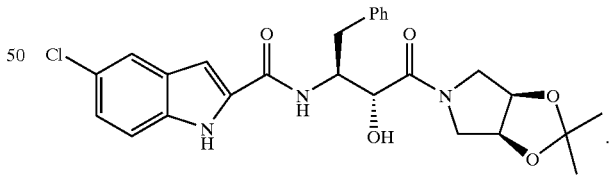

2. A compound of the structural formula

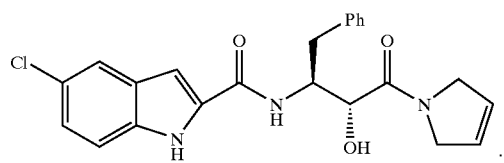

* * * * *